United States Patent [19]
Dobson et al.

[11] Patent Number: 5,687,777
[45] Date of Patent: Nov. 18, 1997

[54] ANESTHETIC AGENT FILLER VALVE

[75] Inventors: Darwin B. Dobson, Sun Prairie; Alan A. Pitas, Evansville, both of Wis.

[73] Assignee: Ohmeda Inc., Liberty Corner, N.J.

[21] Appl. No.: 613,971

[22] Filed: Mar. 11, 1996

[51] Int. Cl.⁶ .................................................. B65B 1/04
[52] U.S. Cl. ........................... 141/18; 141/320; 141/366; 141/367
[58] Field of Search ........................ 141/18, 311 R, 141/320, 349–352, 366, 367, 383, 384, 386; 128/200.19, 200.16, 200.21; 251/149.4, 149.6

[56] References Cited

U.S. PATENT DOCUMENTS

| | | | |
|---|---|---|---|
| 2,989,091 | 6/1961 | Lowenthal | 141/349 |
| 4,862,918 | 9/1989 | Schroeder | 251/149.4 |
| 4,919,125 | 4/1990 | Heaton et al. . | |
| 5,146,915 | 9/1992 | Montgomery . | |
| 5,168,866 | 12/1992 | Montgomery . | |
| 5,170,823 | 12/1992 | Gregory et al. . | |
| 5,381,836 | 1/1995 | Braatz et al. . | |
| 5,505,236 | 4/1996 | Grabenkort et al. . | |

FOREIGN PATENT DOCUMENTS

| | | |
|---|---|---|
| 1193241 | 5/1970 | United Kingdom . |
| 2189472 | 10/1987 | United Kingdom . |

*Primary Examiner*—Robert M. Fetsuga
*Assistant Examiner*—Steven O. Douglas
*Attorney, Agent, or Firm*—Roger M. Rathbun; Salvatore P. Pace

[57] ABSTRACT

An anesthetic vaporizer filler valve is disclosed that can be used in conjunction with anesthetic agent bottles currently commercially available and which have standard keying systems with rotating collars having lugs extending therefrom. The standard collar of such anesthetic agent bottles is keyed into the vaporizer filling valve. the vaporizer filler valve has an internal valve that must be opened in order to introduce the liquid anesthetic agent into the vaporizer sump. By means of a corresponding slot in the vaporizer filler valve that correspond with mating lugs of the standard anesthetic agent bottle, only a proper anesthetic agent bottle can engage and be screwed into the filler valve designed for that specific anesthetic agent.

3 Claims, 5 Drawing Sheets

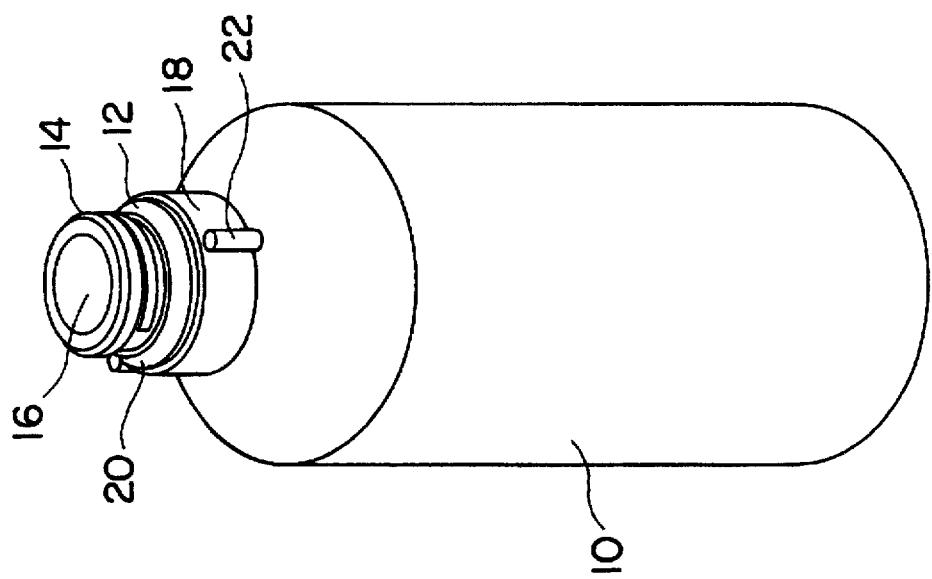
FIG. IA
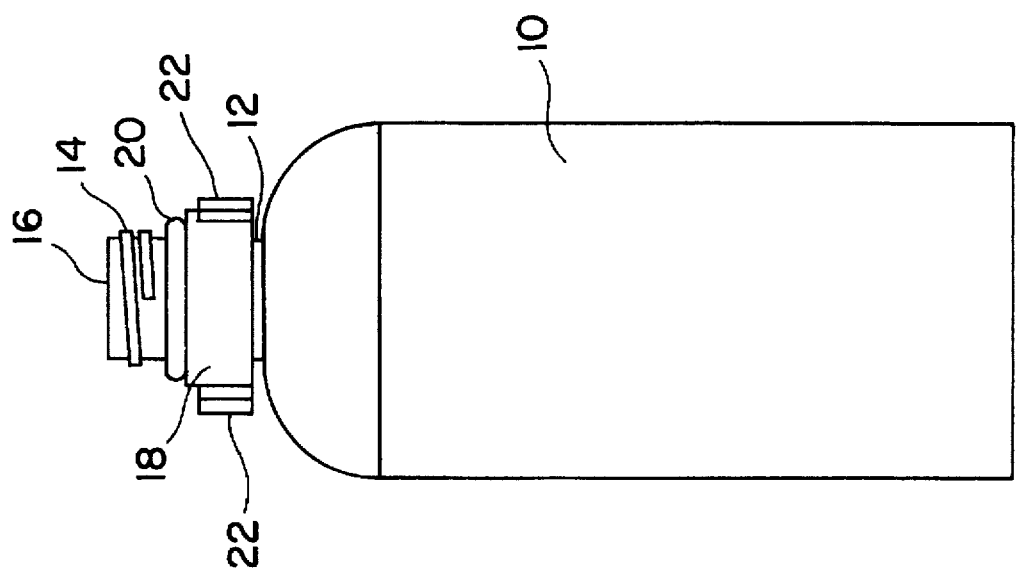
FIG. I

ANESTHETIC AGENT FILLER VALVE

BACKGROUND OF THE INVENTION

This invention relates to a filler valve and mechanism used on an anesthetic vaporizer to introduce liquid anesthetic agent into the sump or reservoir of the vaporizer.

Currently vaporizers are used to vaporize liquid anesthetic agent for administering that agent to a patient in a precise concentration. Typical of such vaporizers are shown and described in U.S. Pat. Nos. 4,919,125; 5,146,915 and 5,168,866.

There are also various keying systems to insure that the proper liquid anesthetic is used with the vaporizer for which it is intended. The introduction of the wrong agent into a vaporizer could result in concentrations of that agent being delivered to the patient different than that intended by the user of the vaporizer.

In addition the various keying arrangements prevent the creation of a cocktail, that is, the mixing of two or more anesthetic agents in the vaporizer and which could result in a unknown concentration of mixed agents to the patient. As such, therefore, the keying system insures that only the proper liquid anesthetic can be introduced into the specific vaporizer designed for that anesthetic.

There is currently in effect standard keying arrangements that are used on the bottle of the liquid anesthetic agents, such as enflurane and isoflurane, and the keying arrangement comprises a plastic collar that freely rotates on the neck of the bottle and which cannot be detached therefrom without deliberate action. That collar has a pair of lugs that are of differing size and differing angular locations around the circumference of the outside of the collar so that the particular bottle is keyed to and can only be used to fill the sump of its mating vaporizer.

At present, the bottle collars are keyed into a filler system where a filler tube is used. One end of the filler tube has slots that key to the lugs on the bottle collar and the other end is keyed in another fashion into the actual vaporizer. The system is disclosed and described in U.K. Patent Number 1193241 and U.K. Published Patent Application Serial No. 2189472, and the keying system disclosed in those publications eliminates the possibility of an anesthetic vaporizer being filled with the wrong anesthetic agent.

As shown in the aforementioned publications, however, the use of an additional tube is somewhat inconvenient and, of course, an additional component is needed. The tube is often misplaced and therefore causes delay in filling a vaporizer. In addition, the additional tube not only needs one keying arrangement but requires two keying arrangements, one on each end of the tube of a differing type. One difficulty of the use of the intermediate tube was disclosed in U.S. Pat. No. 5,170,823 of Gregory et al and a solution offered.

Various other filler valves are employed on anesthetic vaporizers, one of which is shown and described in U.S. Pat. No. 5,381,836 of Braatz et al relating to a specific filling system for a new anesthetic known as desflurane and the disclosure of that U.S. Patent incorporated herein by reference. That particular anesthetic, desflurane, vaporizes readily at or just above ambient temperatures and therefore a special filling system was developed for its use.

Accordingly, the use of a filler valve on an anesthetic vaporizer that opens up to fill the vaporizer upon rotation of the valve is shown in the aforementioned patent, however, that system utilizes a valve in the bottle itself and a further check valve in the filler valve that is opened when a special shaped bottle end is inserted into the anesthetic vaporizer filler valve. As such, the system of that patent is not applicable to be used with the current available bottles used with either enflurane or isoflurane having the previously described rotating collar that is part of a safety keying system.

SUMMARY OF THE INVENTION

In accordance with the present invention, an anesthetic vaporizer filling system is adaptable for use with the present bottles having the standardized rotating collars with lugs, however, the present system allows the anesthetic agent bottle to be inserted directly into the anesthetic vaporizer without the need for an intermediate tube. The filling system provides a keying arrangement on the vaporizer filler valve such that the bottle cannot be affixed to the vaporizer and emptied into that vaporizer unless the standard keying arrangement on the anesthetic agent bottle mates with the keying system on the vaporizer filler valve.

Accordingly, the standard keying arrangement currently used on the commercial anesthetic agent bottles can be retained and those bottles used to directly fill the anesthetic vaporizer without the need for an intermediate tube, yet the corresponding mated keying arrangement on the vaporizer filler valve will insure that only the proper anesthetic agent can be introduced into that vaporizer.

Other objects, features and advantages of the present invention will be more apparent from the detailed description of the preferred embodiments set forth below, taken in conjunction with the accompanying drawings.

BRIEF DESCRIPTION OF THE DRAWINGS

FIGS. 1 and 1A are front views and perspective views, respectively, of the standard anesthetic agent bottle and showing the conventional keying collar;

DESCRIPTION OF THE PREFERRED EMBODIMENT

Figure 2:
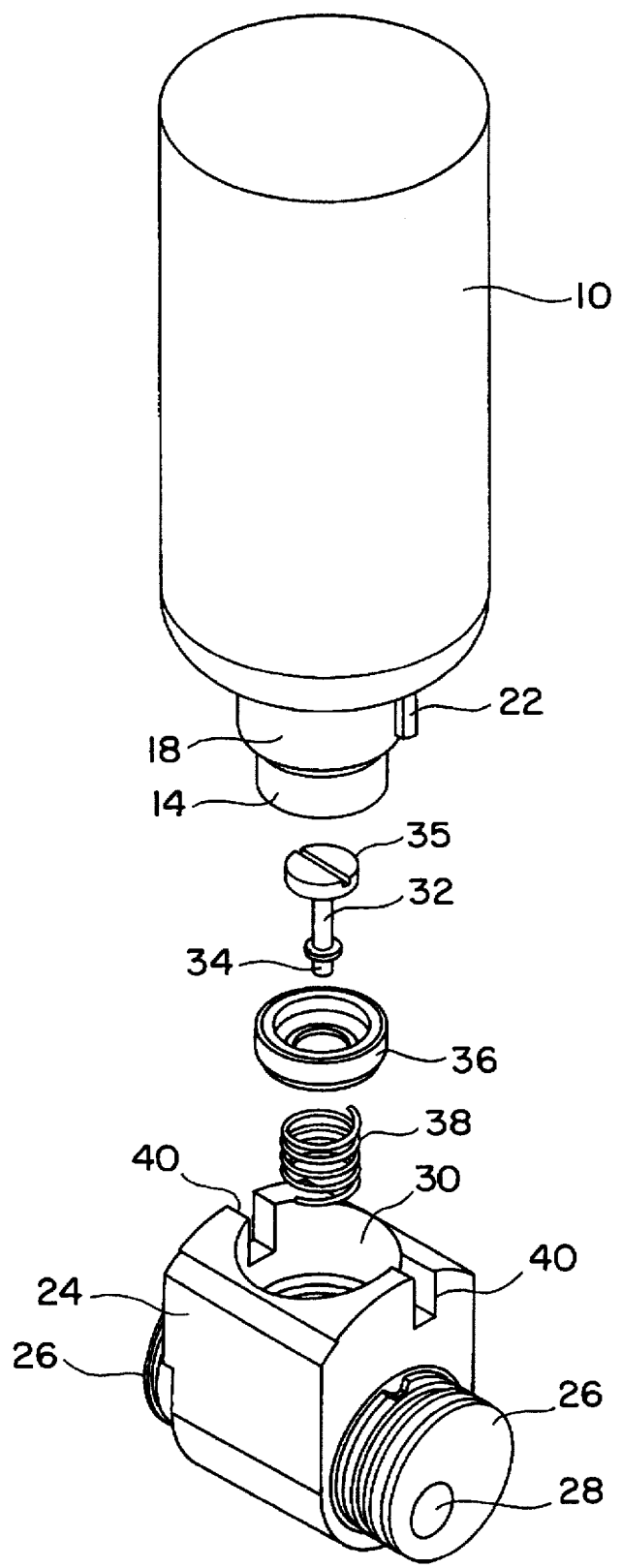
FIG. 2 is an exploded view of a conventional anesthetic agent bottle and a vaporizer filler valve constructed in accordance with the present invention.

Turning first to FIGS. 1 and 1A, there is shown a side view and a perspective view of a conventional anesthetic agent bottle currently on the market. Typically the bottle is used for the volatile anesthetic agents enflurane and isoflurane marketed commercially under the trademarks Ethrane and Forane, respectively.

As shown the anesthetic agent bottle 10 has a neck 12 extending therefrom with a threaded end 14 having an opening 16 for mating with the threads of the particular vessel into which the anesthetic agent is to be poured. Surrounding the neck 12 is a collar 18 that is allowed to rotate freely about the neck 12 but is constrained from being removed therefrom by means such as a bead 20.

The collar 18 is generally a plastic molding and has lugs 22 extending from collar 18 of a specific size and location about the circumference of the collar 18. The location and size of the lugs 22 is determined by the particular anesthetic agent contained within that bottle. As can be seen in the aforementioned U.K. Patent and Patent application, the location and size of the lugs 22 are arranged such as to be keyed into corresponding slots of the same size and location in the mating fitting of the filler tube so that the tube can only be used with a bottle having a specific anesthetic agent. As stated, the particular collar has been standardized for each of the anesthetic agents supplied with that particular keying system.

Turning now to FIG. 2, there is shown an exploded view of a conventional anesthetic agent bottle 10 and a vaporizer filler valve constructed in accordance with the present invention. The vaporizer filler valve is comprised of a valve block 24 that may be made of a material such as brass. Extending outwardly from each side of the valve block 24 are valve fittings 26, the purpose of which will be later disclosed. An outlet port 28 is formed in one of the valve block fittings 26 as shown in the FIG.2. A central bore 30 is formed in the valve block 24 and which is adapted to be dimensioned to receive the collar 18 of the bottle container 10.

An internal valve is provided within the valve block 24 and comprises a fixed valve seat 32 located within the central bore 30 and which preferably has a threaded end 34 for affixing the same into the valve block 24 The other end of the fixed valve seat 32 is shaped as an enlarged end 35 and which is slotted to receive a screwdriver for threading the fixed valve seat 32 into its operative position to valve block 24. A movable valve member 36, preferable of a plastic material such as Teflon, also is eventually contained with in the central bore 30 of the valve block 24 as will be described. A spring 38 acts to bias the movable valve member 36 to its closed position against the fixed valve seat 32 when assembled.

As also can be noted in FIG. 2, slots 40 are formed in the valve block 24 and which are sized and located around the periphery of the central bore 30 so as to receive the lugs 22 formed on the collar 18 of the bottle container 10 such that the particular spacing and size of the lugs 22, specific for a particular anaesthetic agent, must mate with the corresponding slots 40 within the valve block 24 in order to provide an operational system to fill an anesthetic vaporizer with the specific anesthetic agent.

Figure 3:
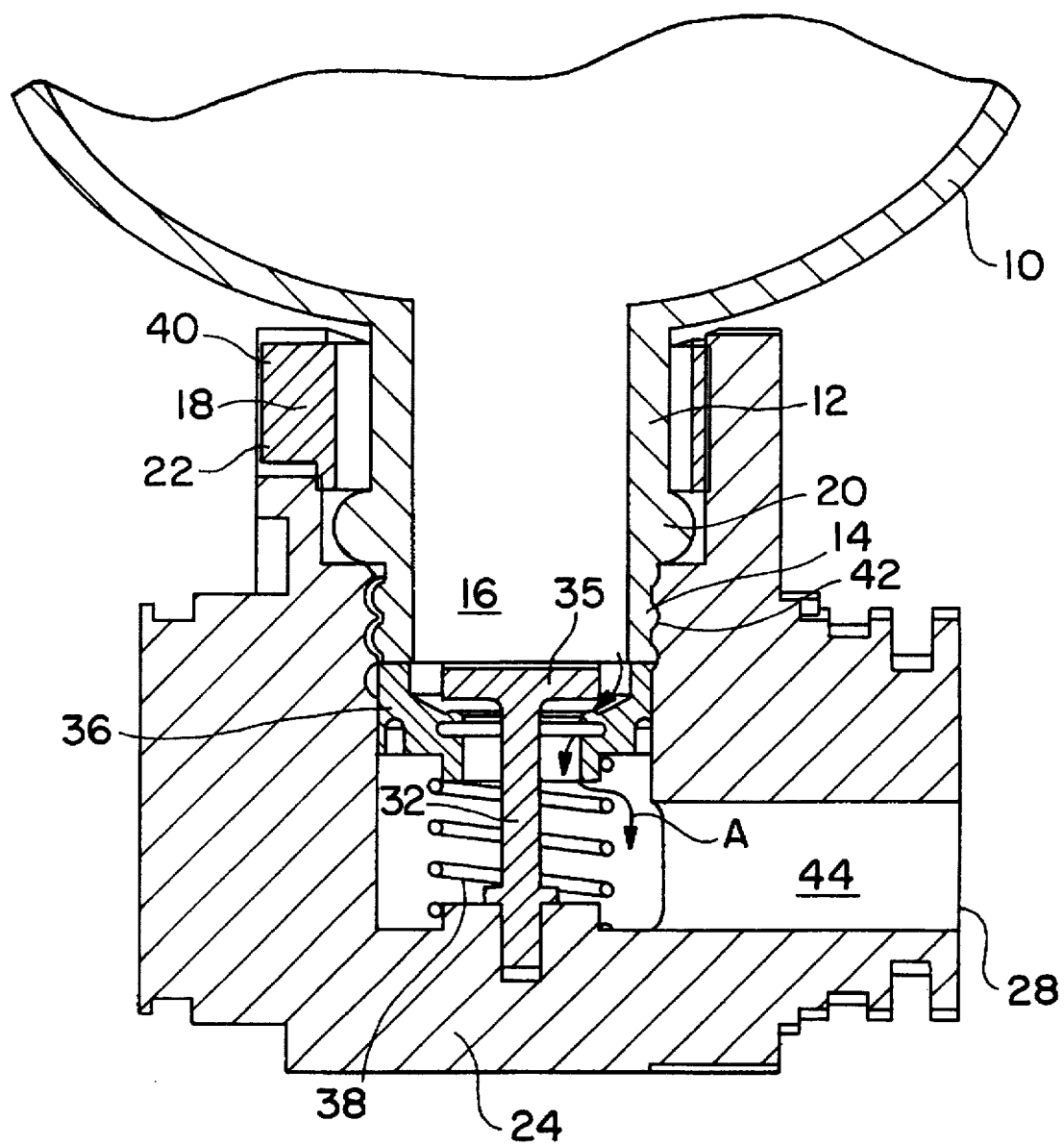
FIG. 3 is a side sectional view of the vaporizer filler valve of FIG. 2.

Turning now to FIG. 3, there is shown a side sectional view of the vaporizer filler valve of the present invention, In FIG. 3, it can be seen that the valve block 24 has it's central bore 30 receiving the anesthetic agent bottle 10 such that the lugs 22 of the anesthetic agent bottle 10 interfit with the slots 40 in the valve block 24. The threaded end 14 of anesthetic agent bottle 10 is screwed into internal threads 42 formed in the central bore 30 such the anesthetic agent bottle 10 can be engaged to the valve block 24.

As also can be seen, the fixed valve seat 32 is affixed to the bottom of the central bore 30 and extends upwardly therefrom. Movable valve member 36 is shown in the open position displaced away from the enlarged end 35 of the fixed valve seat 32 so that liquid can pass from the bottle container 10, through the filler valve in the direction of the arrows A and outwardly through passageway 44 and thus through the outlet port 28. When, of course, the bottle container 10 is unscrewed from the valve block 24, the spring 38 exerts its bias in the upward direction and causes the movable valve member 36 to seat against the lower surface of the enlarged end 35 of fixed valve seat 32 thereby closing the filler valve to the passage of liquid.

In the operation of the anesthetic vaporizer filling system of the present invention, therefore, the anesthetic agent bottle 10 containing a specific anesthetic is inserted into the central bore 30 of the valve block 24. The anesthetic agent bottle 10 is then rotated to cause the threaded end 14 of anesthetic agent bottle 10 to engage the internal threads 42 of the central bore 30 and the anesthetic agent bottle 10 is advanced into the central bore 30 as the anesthetic agent bottle is rotated.

As the anesthetic agent bottle 10 advances, the filler valve is opened by the threaded end 14 of the anesthetic agent bottle 10 engaging the upper surface of movable valve member 36 and moving that valve member against the bias of spring 38 to a position away from the fixed valve seat 32 to allow liquid anesthetic to pass from the anesthetic agent bottle 10 through the filler valve and outwardly through the passageway 44 to exit via the outlet port 28.

Obviously, the ability to open the filler valve depends upon the engagement of the threaded end 14 of the anesthetic agent bottle 10 with the upper surface of the movable valve member 36 and the system is dimensioned such that the lugs 22 of the anesthetic agent bottle 10 must enter the mating slots 40 of the valve block in order to allow the threaded end 14 of the anesthetic agent bottle 10 to advance sufficiently to engage the internal threads 42.

Therefore, an anesthetic agent bottle having the standard keyed collar 18 can be used and the same safety effected since the filler valve will only allow the proper specific anesthetic agent to enter the filling valve and thus fill the sump of the vaporizer. That is, if the proper collar 18 does not mate with the corresponding slots 40, the anesthetic agent bottle 10 cannot engage the internal threads 42 and thus the system will not be operable to receive the anesthetic agent from that particular bottle.

Figure 4:
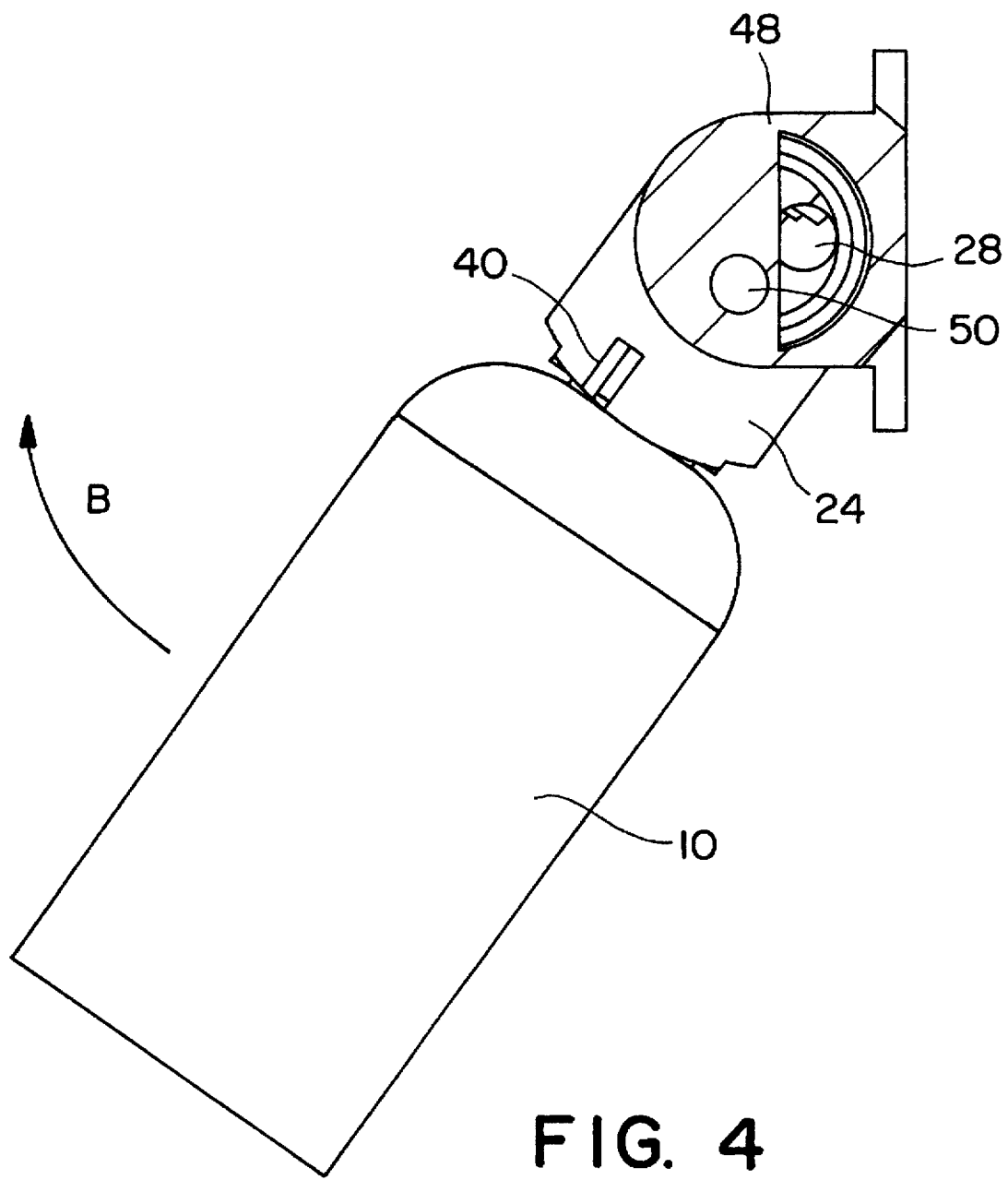
FIG. 4 is a side view, partly in section, showing an anesthetic agent bottle in place in the vaporizer filler valve of the present invention.
Figure 5:
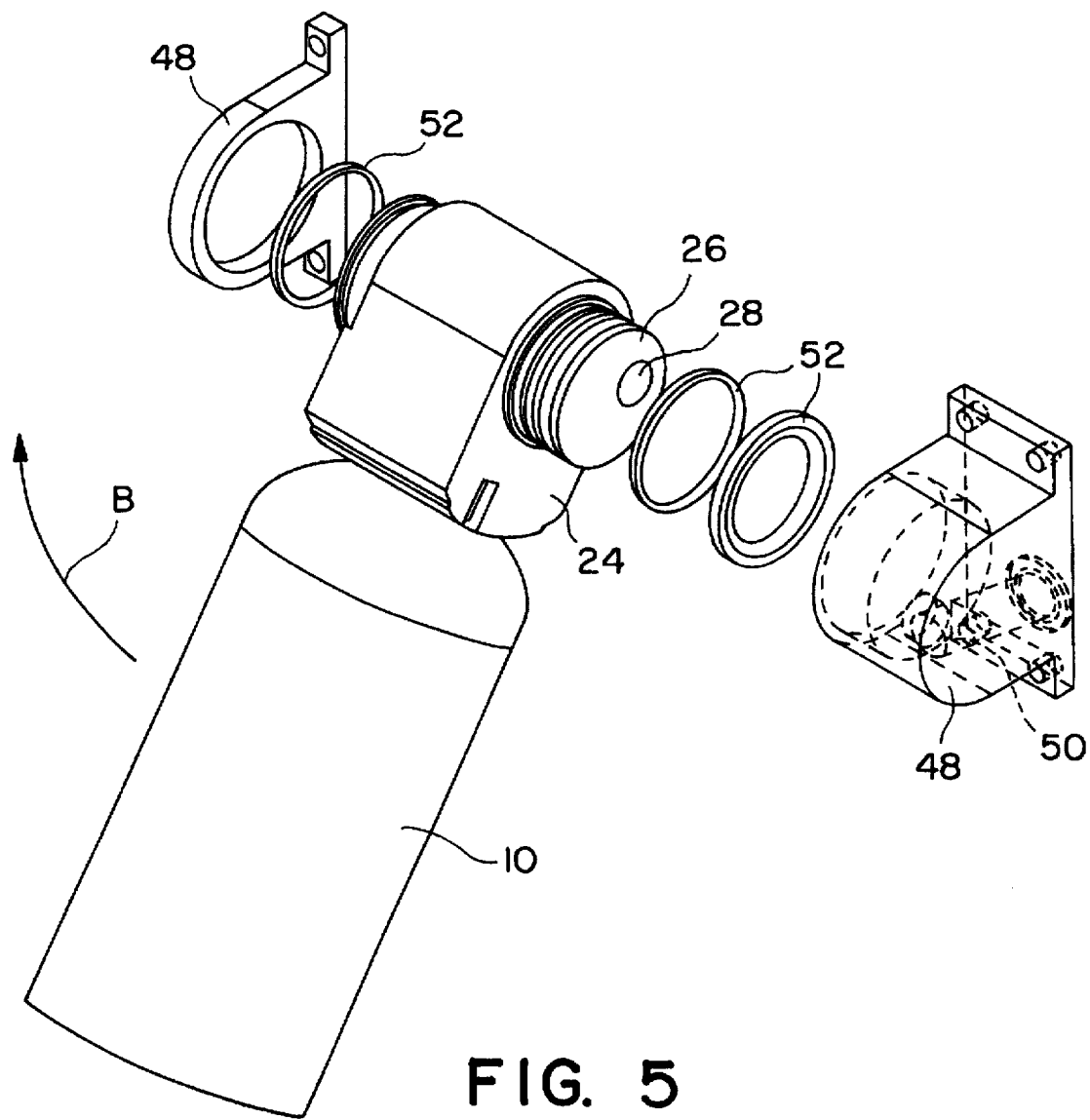
FIG. 5 is an exploded perspective of the anesthetic agent bottle and vaporizer filler valve of the present invention.

Finally, taking FIGS. 4 and 5 together, there is shown, respectively, a side view and an exploded view of the filling system of the present invention. As can be seen, the valve fittings 26 are fitted within vaporizer mounting blocks 48 that are mounted to the side of an anesthetic vaporizer, not shown. The anesthetic agent bottle 10 is shown in both FIGS. in its downward, closed position such that the outlet port 28 in the valve block 24 does not align with the passageway 50 in the vaporizer mounting block 48. Accordingly, in the position shown, the anesthetic agent bottle 10 can be affixed to the filler valve such that the internal filler valve is opened as previously explained, yet the anesthetic agent still cannot flow into the vaporizer in the shown position.

The valve block 24 is, however pivotally affixed to the vaporizer mounting blocks 48 and is sealed within the vaporizer mounting blocks 48 by a series of seals 52. As the bottle container 10 is pivoted by the user in the direction of the arrow B, however, the outlet port 28 of the valve block 24 rotates so as to eventually become aligned with the passageway 50 in vaporizer valve block 48, there by allowing the liquid anesthetic to pass from the bottle container 10 to enter the sump or reservoir of the vaporizer.

While the present invention has been set forth in terms of a specific embodiment, it will be understood that the anesthetic vaporizer filling system herein disclosed may be modified or altered by those skilled in the art to other configurations. Accordingly, the invention is to be broadly construed and limited only by the scope and spirit of the claims appended hereto.

We claim:

1. A filler valve for use with an anesthetic vaporizer and adapted to receive an anesthetic agent bottle having external threads and having a pair of projecting lugs rotatably mounted thereto, said filler valve comprising a housing, said housing having an inlet having internal threads mating with the external threads of an anesthetic agent bottle and an outlet, a valve within said housing intermediate said inlet and said outlet and having a fixed seat and a movable member, bias means to bias said movable valve member toward said fixed seat to close said valve, said inlet having a pair of slots adapted to slidingly receive said pair of lugs when properly aligned to allow the bottle to enter said inlet, said inlet being dimensioned whereby the anesthetic agent bottle moves said movable valve member away from said fixed seat by the action of the anesthetic agent bottle entering said inlet by being screwed to said inlet and the anesthetic agent bottle being prevented from entering said inlet to open said valve when said pair of lugs on the anesthetic agent bottle do not align with said pair of slots in said inlet.

2. A filler valve as defined in claim 1 wherein said movable valve member is spring biased and said spring is compressed by said bottle entering said inlet.

3. A vaporizer filling system comprising the combination of an anesthetic agent bottle, a collar and a filler valve of an anesthetic vaporizer, said collar being arranged and freely rotatable around the neck of the anesthetic agent bottle and formed with a plurality of axially extending lugs, said filler valve having an outlet and an inlet having internal screw threads and said anesthetic agent bottle having mating circumferential extending screw threads, said filler valve having a plurality of axially extending slots for receiving said plurality of axially extending lugs of said collar, a passageway within said filler valve for receiving liquid from said anesthetic agent bottle when positioned within said inlet of said filler valve to provide liquid anesthetic agent to said outlet port, an internal valve within said filler valve controlling the flow of liquid through said passageway, said internal valve having a fixed valve seat and a movable valve member having an open position where liquid can pass therethrough and a closed position blocking the flow of liquid through said passageway, bias means biasing said movable valve member to said closed position, said anesthetic agent bottle and said filler valve being dimensioned such that said bottle opens said internal valve when said anesthetic agent bottle is threadedly engaged with said inlet, said threaded engagement being permitted only when said plurality of lugs are properly aligned with said plurality of slots in said inlet of said filler valve.

* * * * *